United States Patent [19]

Bouillon et al.

[11] 4,209,506
[45] Jun. 24, 1980

[54] ALUMINUM TRIS-(N-OXYPYRIDINE-2-THIOLATE); COSMETIC OR PHARMACEUTICAL COMPOSITIONS CONTAINING THE SAME AND THE USE OF SAID COMPOSITIONS

[75] Inventors: Claude Bouillon, Eaubonne; Georges Rosenbaum, Asnieres, both of France

[73] Assignee: L'Oreal, Paris, France

[21] Appl. No.: 928,312

[22] Filed: Jul. 26, 1978

[30] Foreign Application Priority Data

Jul. 28, 1977 [FR] France .................................. 77 23261

[51] Int. Cl.$^2$ ................... C07D 213/89; A61K 31/44; A61K 7/38
[52] U.S. Cl. ........................................ 424/68; 424/46; 424/47; 424/69; 424/70; 424/245; 424/DIG. 5; 546/6; 426/532

[58] Field of Search ............. 260/270 R; 424/46, 245, 424/47, 68, 70, 69, DIG. 5; 426/532; 546/6

[56] References Cited

U.S. PATENT DOCUMENTS

| 3,347,863 | 10/1967 | Ottman | 260/270 R |
| 3,953,450 | 4/1976 | Bouillon et al. | 424/68 |
| 4,072,742 | 2/1978 | Bouillon et al. | 424/68 |

*Primary Examiner*—Mark L. Berch
*Attorney, Agent, or Firm*—Cushman, Darby & Cushman

[57] ABSTRACT

Aluminum tris(N-oxypyridine-2-thiolate) is useful in the prophylaxis or treatment of any pathological manifestation in which the presence of a microorganism is involved. It is a new compound made by the reaction of aluminum isopropylate with the N-oxide of pyridine-2-thiol.

15 Claims, No Drawings

ALUMINUM TRIS-(N-OXYPYRIDINE-2-THIOLATE); COSMETIC OR PHARMACEUTICAL COMPOSITIONS CONTAINING THE SAME AND THE USE OF SAID COMPOSITIONS

The present invention relates to sulphur-containing aluminum salts, their preparation and cosmetic and pharmaceutical compositions containing them.

In U.S. Pat. No. 3,953,450 and 4,072,742, sulphur-containing aluminum salts possessing anti-microbial properties have been described. These compounds have been used mainly in deodorant/anti-perspirant and anti-dandruff compositions and also in compositions for body care and, in particular, for feminine hygiene. However, although these compounds exhibit an excellent activity, their field of use has been limited by their low solubility in water and alcohol.

The present invention provides a new sulphur-containing aluminum salt which possesses a greater solubility and also an excellent activity and consequently makes possible the production of a wide variety of cosmetic and pharmaceutical compositions.

The new salt of the present invention is aluminum tris-(N-oxypyridine-2-thiolate), which has the following formula:

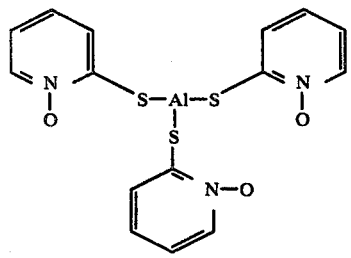

This compound forms a whitish powder. Its molecular weight is: $C_{15}H_{12}N_3O_3S_3Al = 405$.

This compound exhibits an excellent activity towards Gram(+) bacteria such as *Staphylococcus aureus*, *Bacillus subtilis* and *Micrococcus luteus*, and Gram(−) bacteria such as *Escherichia coli*, *Klebsiella pneumoniae* and *Pseudomonas aeruginosa*, towards yeasts such as *Saccharomyces cerevisiae* and *Candida lipolytica*, and also towards moulds such as *Aspergillus niger* and *Penicillium notatum*.

According to a feature of the invention, aluminum tris-(N-oxypyridine-2-thiolate) is prepared in accordance with the following equation:

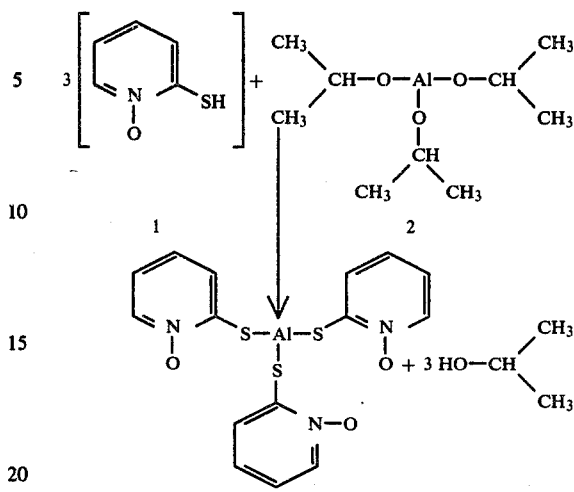

Thus, aluminum isopropylate (2) is reacted with three molar equivalents of the N-oxide of pyridine-2-thiol (1). The reaction is carried out in an anhydrous solvent which is preferably an aromatic hydrocarbon such as benzene or toluene, a chlorinated solvent such as dichloroethane or chloroform, or an alcohol such as isopropanol.

In this process, it is not necessary to supply heat, but it is possible to accelerate the reaction rate by the action of moderate heat so that the reaction temperature is 20° C. to 100° C.

The active product is subsequently isolated by evaporating the solvent under reduced pressure.

The present invention also provides cosmetic and pharmaceutical compositions in which aluminium tris-(N-oxypyridine-2-thiolate) (I) is the active ingredient. The latter is preferably used by itself or, optionally, in admixture with other active principles and, in particular, in association with aluminum tri-(camphor-10-sulphonate).

In fact, it has been found that, by associating aluminum tris-(N-oxypyridine-2-thiolate) with aluminum tri-(camphor-10-sulphonate), it is possible further to increase the solubility of the active compound of the invention. Thus, by adding about 3% of aluminum tri-(camphor-10-sulphonate), it is possible to double the solubility of aluminum tris-(N-oxypyridine-2-thiolate).

When taken by itself or in association with another active principle, and especially with aluminum tri-(camphor-10-sulphonate), the active compound according to the invention can be incorporated into many cosmetic or therapeutic compositions which are intended either for hygiene or for the treatment of warm-blooded animals (including man), both by local application and by oral administration. More particularly, the active compound according to the invention can be used in deodorant, disinfectant and antiseptic compositions which are intended for body hygiene, personal hygiene, the hygiene of the scalp and, in general, the hygiene and care of the integuments and superficial body growths, in anti-dandruff, anti-acne and anti-mycosis compositions and, in general, in compositions which are intended for prophylaxis or the treatment of any pathological manifestation in which the presence of a micro-organism is involved, such as, for example, pityriasis, onyxis, intertrigos, dermatomycosis, dermatophytosis, impetigo, dermatosis with a secondary infection, athlete's foot, pruritus of infectious origin, hyperhidrosis or parasitosis.

The active compound according to the invention can also be used as preservative.

The compositions, according to the invention, for local application generally contain from 0.01 to 10% by weight, and preferably from 0.05 to 3%, of the active compound according to the invention.

These compositions for local application can be in various forms and, in particular, in the form of a liquid shampoo, a dry shampoo, a lotion, a cream, a milk, a stick, a powder, a soap, a gel, an ointment or an alcoholic, dry or powder spray.

The creams are preferably emulsions of the "oil-in-water" type consisting of about 10–50% of oil and 90–50% of water.

Amongst the oils which can be employed for forming the oily phase of the emulsions, there may be mentioned, in particular; hydrocarbon oils such as paraffin oil, purcellin oil, perhydrosqualene and solutions of microcrystalline wax in oils, animal or vegetable oils such as sweet-almond oil, avocado oil, calophyllum oil, lanoline, castor oil, caballine oil, lard oil and olive oil, mineral oils having an initial distillation temperature at atmospheric pressure of about 250° C. and a final distillation temperature of the order of 410° C. and saturated esters such as isopropyl palmitate, alkyl myristates such as isopropyl, butyl and cetyl myristates, hexadecyl stearate, ethyl palmitate, the triglycerides of octanoic and decanoic acids and cetyl ricinoleate.

Silicone oils which are soluble in the other oils, such as dimethylpolysiloxane, methylphenylpolysiloxane and silicone/glycol copolymer can also be used in the oily phase.

In order to assist retention of the oils, the oily phase can also contain waxes such as carnauba wax, candelilla wax, beeswax, microcrystalline wax and ozokerite.

It is also possible to use fatty alcohols such as stearyl alcohol, cetyl alcohol and 2-octyldodecan-1-ol, oxyethyleneated fatty alcohols and propylene glycol for producing the creams according to the invention.

When the compositions according to the invention are in the form of sticks, the latter consist of molten waxes in which an aqueous, alcoholic or aqueous-alcoholic solution or suspension of the active compound as defined above is incorporated in the form of an emulsion.

It is also possible to introduce certain amounts of oils or fatty alcohols into the waxes. In general, the waxes, oils and fatty alcohols used for producing sticks according to the invention are the same as those mentioned above for producing the creams.

The emulsifiers can be conventional emulsifiers for this type of composition and, in particular, fatty amides such as copra monoethanolamide, stearyl diethanolamide and the like.

The compositions, according to the invention, in the form of a powder can contain talc or any other similar substance and also a certain amount of fatty material which makes it possible to agglomerate the powder obtained.

The compositions according to the invention can also be in the form of aerosol sprays. These sprays can be either alcoholic sprays or dry sprays or also powder sprays. In this production form, the concentration of active compound is generally between 0.01 and 5% by weight, relative to the total weight of the aerosol composition.

The alcoholic sprays in the form of aerosols contain, in addition to the active compound, an anhydrous alcohol taken from the group comprising ethanol and isopropanol, and one or more propellants such as fluorochlorinated hydrocarbons, volatile hydrocarbons, carbon dioxide gas, nitrous oxide or also nitrogen. They can also be associated with methylene chloride.

The compositions, according to the invention, in the form of dry sprays contain, in addition to the active compound and the propellant liquefied under pressure, talc or any other similar substance associated with a certain amount of fatty material such as oils or fatty alcohols.

Of course, the compositions, according to the invention, for local administration can also contain other conventional ingredients such as, for example, penetrating agents, perfumes, colorants or thickeners.

The compositions, according to the invention, for oral administration can be in various forms and, in particular, in the form of tablets, dragees, capsules, pills, powder, granules, sugar-coated capsules, boles, potions, suspensions or solutions and preferably contain the active compound in an amount of between 0.01 and 80%.

Oral administration can be carried out either as a cure or, in smaller doses, for prophylaxis. The unit dose of active ingredient can be between 0.001 and 200 mg/kg, depending on the animal or the person to be treated and on the nature of the infection to be treated.

When the compositions according to the invention are to be in solid form, the active compound is ground into a fine powder which is mixed with a diluent of the kind which is ordinarily used in pharmaceutical or veterinary formulation. Amongst the diluents used, there may be mentioned starch, lactose, talc, magnesium stearate, vegetable gums, pectin, dextrin, agar, calcium phosphate, kaolin and bentonite.

If desired, it is also possible to incorporate a sweetening agent such as, for example, sugar or an aromatic oil. The tablets or dragees can be coated, in accordance with the usual techniques, so as to form a coating which is insoluble in the gastric juices but soluble in the intestinal juices.

When the composition is in the form of a capsule or sugar-coated capsule, the active compound is incorporated inside a hard or soft gelatine envelope or any form of encapsulation which is acceptable from a pharmaceutical point of view.

The solutions or suspensions of active compound can be produced in water, in an alcohol such as ethanol, propylene glycol, glycerol, sorbitol, ethyldiglycol or butyldiglycol, or in pyrrolidone, an N-alkylpyrrolidone or an N,N-dialkylacetamide, by themselves or in a mixture.

As the liquid excipient, it is also possible to use vegetable oils such as groundnut oil, olive oil, corn oil, sesame oil or the like.

The potions can be in the form of a solid to be diluted in water at the time of administration and they can also contain surface-active agents which assist dissolution or emulsion formation.

The active compound according to the invention can also be incorporated as an additive into composite feedstuffs for animal feeding.

In this case, the active compound is associated with edible excipients and there may be mentioned, in particular, soya cake, cottonseed cake, linseed cake or sunflower cake, corn gluten flour, cornflour, wheat flour, fish meal, citrus fruit meal or bonemeal, limestone, ground oyster shells or ground eggshells, soya meal, soluble extracts of molasses, by-products of the milling industry, or the like. According to this production form, the active compound is generally present in the feedstuff in an amount of 1 to 2,000 ppm by weight. When it is incorporated in a prediluted form, its concentration in the premixture can be from 0.1 to 20% by weight.

When aluminum tri-(camphor-10-sulphonate) is used in a mixture with the active compound according to the invention, its concentration is generally between 0.05 and 30%.

An example of the preparation of the active compound according to the invention, and also various examples of cosmetic and pharmaceutical compositions in which it is present, will now be given by way of illustration and without implying any limitation.

Preparation of aluminum tris-(N-oxypyridinethiolate) (I)

20.4 g (0.1 mol) of aluminum isopropylate are dissolved in 200 ml of dichloroethane. 38.1 g (0.3 mol) of the N-oxide of pyridine-2-thiol are added, whilst stirring. After the exothermic reaction has ended (about a quarter of an hour), the mixture is heated under reflux for two hours. It is then concentrated to dryness under reduced pressure. 40.3 g of the expected active product are thus collected in the form of a whitish powder (expected theoretical weight: 40.5 g).

Analysis: Al calculated % 6.66; found % 6.70.

Preparation of aluminum tri-(camphor-10-

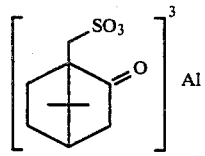

sulphonate)

69.6 g (0.3 mol) of camphor-10-sulphonic acid are added, whilst stirring vigorously, to a solution of 20.4 g (0.1 mol) of aluminum isopropylate in 200 ml of anhydrous isopropanol. The stirring is continued for about 30 minutes and the reaction mixture is then heated under reflux for 90 minutes. The solvent is evaporated off under reduced pressure in a rotary evaporator and the residual solid obtained is dried to constant weight in an oven at 115° C.

72 g of a white solid of crystalline appearance are thus obtained (theoretical weight 72 g).

Analysis: Al calculated % 3.74; found % 3.70.

COMPOSITION EXAMPLES

EXAMPLE 1

A deodorant lotion having an anti-dandruff and antiseptic action is prepared according to the invention by mixing the following ingredients:

| Aluminum tris-(N-oxypyridinethiolate) | 0.05 | g |
| Aluminum tri-(camphor-10-sulphonate) | 0.1 | g |
| Menthol | 0.05 | g |
| Ethanol | 50 | g |
| Water q.s.p. | 100 | g |

On applying this composition to a head of hair with dandruff, a reduction in the formation of dandruff is found after a daily treatment lasting 15 days.

EXAMPLE 2

A deodorant cream is prepared according to the invention by mixing the following ingredients:

| Oxyethyleneated cetyl/stearyl alcohol containing | |
|---|---|
| 15 mols of ethylene oxide | 10g |
| Cetyl alcohol | 2g |
| Spermaceti | 2g |
| Vaseline oil | 5g |
| Sweet-almond oil | 1g |
| Essential oil of rosemary | 0.2g |
| Essential oil of lavender | 0.3g |
| Geranium oil | 0.1g |
| Aluminum tris-(N-oxypyridinethiolate) | 0.15g |
| Water q.s.p. | 100g |

When applied regularly, this cream makes it possible to prevent the formation of bad odors.

EXAMPLE 3

A deodorant cream for the care of the feet is prepared according to the invention by mixing the following ingredients:

| Self-emulsifying glycerol stearate | 6 g |
|---|---|
| Stearic acid | 2 g |
| Castor oil | 2 g |
| Vaseline oil | 5 g |
| Isopropyl myristate | 3 g |
| Allantoin | 0.3 g |
| Camphor | 0.3 g |
| Menthol | 0.2 g |
| Aluminum tris-(N-oxypyridinethiolate) | 0.6 g |
| Aluminum tri-(camphor-10-sulphonate) | 2.4 g |
| Water q.s.p. | 100 g |

EXAMPLE 4

An emulsion suitable for a roll-on applicator and having a deodorant and antiseptic action is prepared according to the invention by mixing the following ingredients:

| Lauryl alcohol oxyethyleneated with 2 to | |
|---|---|
| 3 mols of ethylene oxide | 0.5 g |
| Vaseline oil | 2.5 g |
| Lanoline | 1 g |
| Higher fatty alcohols (50/50 mixture of stearyl alcohol and cetyl alcohol) | 1.5 g |
| Corn starch | 2 g |
| Aluminum tris-(N-oxypyridinethiolate) | 0.1 g |
| Aluminum tri-(camphor-10-sulphonate) | 0.1 g |
| Water q.s.p. | 100 g |

EXAMPLE 5

A deodorant milk is prepared according to the invention by mixing the following ingredients:

| Magnesium lauryl-sulphate | 20 g |
|---|---|
| Colloidal silica | 6 g |
| Glycerides of fatty acids ($C_{14}$ to $C_{18}$) | 5 g |
| Aluminum tris-(N-oxypryridinethiolate) | 0.2 g |
| Micro-encapsulated perfume | 20 g |
| Whole milk powder q.s.p. | 100 g |

EXAMPLE 6

A deodorant and antiseptic body lotion for dry skin is prepared according to the invention by mixing the following ingredients:

| | |
|---|---|
| Aluminum tris-(N-oxypyridinethiolate) | 0.5 g |
| Aluminum tri-(camphor-10-sulphonate) | 2 g |
| Keratin proteolysis product | 10 g |
| d-1 Norvaline | 0.5 g |
| Aqueous placental extract | 5 g |
| Sodium alginate | 0.5 g |
| Vaseline oil | 5 g |
| Lanoline | 1 g |
| Polyoxyethyleneated oleyl alcohol | 5 g |
| Water q.s.p. | 100 g |

EXAMPLE 7

A protective and disinfectant spray is prepared according to the invention by mixing the following ingredients:

| | |
|---|---|
| Ethyl p-aminobenzoate | 0.5 g |
| Ethylhexyl adipate | 10.3 g |
| Wheatgerm oil | 1 g |
| Azulene | 0.10 g |
| Aluminum tris-(N-oxypyridinethiolate) | 0.05 g |
| Aluminum tri-(camphor-10-sulphonate) | 0.1 g |
| Ethanol | 80 g |

This mixture is then packaged in an aerosol container in the presence of $CO_2$ so as bring the internal pressure to 8 bars.

EXAMPLE 8

A powder spray for the care of the feet is prepared according to the invention by mixing the following ingredients:

| | |
|---|---|
| Aluminum tris-(N-oxypyridinethiolate) | 2 g |
| Titanium oxide | 5 g |
| Kaolin | 5 g |
| Lavender oil | 1 g |
| Talc (20 microns) q.s.p. | 100 g |

10 g of this composition are packaged in an aerosol bottle in the presence of 54 g of trichlorofluoromethane and 36 g of dichlorodifluoromethane.

EXAMPLE 9

An antiseptic and cicatrizant talc is prepared according to the invention by mixing the following ingredients:

| | |
|---|---|
| Magnesium stearate | 5 g |
| Zinc oxide | 5 g |
| Boric acid | 2 g |
| Undecylenic acid | 0.2 g |
| Aluminum tris-(N-oxypyridinethiolate) | 3 g |
| Talc q.s.p. | 100 g |

EXAMPLE 10

A deodorant and antiseptic composition for impregnating fabrics intended for feminine hygiene is prepared according to the invention by mixing the following ingredients:

| | |
|---|---|
| Aluminum tris-(N-oxypyridinethiolate) | 0.1 g |
| Aluminum tri-(camphor-10-sulphonate) | 0.1 g |
| Ethanol | 70 g |
| Perfume q.s. | 1 g |
| Water q.s.p. | 100 g |

EXAMPLE 11

An anti-acne milk is prepared according to the invention by mixing the following ingredients:

| | |
|---|---|
| Polyoxyethyleneated cetyl/stearyl alcohol | 2.6 g |
| Cetyl alcohol | 2.6 g |
| t-Butyl-hydroxyanisole | 0.01 g |
| Stearic acid | 1.6 g |
| Mineral oil | 6.85 g |
| Vegetable oil | 1.3 g |
| Polyoxyethyleneated derivative of sorbitol | 0.26 g |
| Isopropyl myristate | 4.5 g |
| Perfume q.s. | 0.3 g |
| 5-Amino-3-thiahexanedioic acid | 1 g |
| Aluminum tris-(N-oxypyridinethiolate) | 0.7 g |
| Aluminum tri-(camphor-10-sulphonate) | 3 g |
| Triethanolamine q.s.p. pH 4.2 | |
| Water q.s.p. | 100 g |

EXAMPLE 12

An anti-acne cream is prepared according to the invention by the mixing the following ingredients:

| | |
|---|---|
| Cetyl alcohol | 7 g |
| Mineral oil | 5 g |
| Stearic acid | 2 g |
| Polyoxyethyleneated derivative of sorbitol | 16 g |
| Allantoin | 0.3 g |
| Azulene | 0.1 g |
| Aluminum tris-(N-oxypyridinethiolate) | 0.7 g |
| Aluminum tri-(camphor-10-sulphonate) | 3 g |
| Water q.s.p. | 100 g |

On applying this cream regularly at night, it is found that the appearance of the skin improves and acne rashes disappear.

EXAMPLE 13

Tablets for countering infections due to germs or parasites are prepared according to the invention by mixing the following ingredients:

| | |
|---|---|
| Lactose | 150 mg |
| Gum arabic | 100 mg |
| Starch | 100 mg |
| Aluminum tris-(N-oxypyridinethiolate) | 10 mg |

EXAMPLE 14

A lotion, to be used daily, for countering dandruff or parasites is prepared according to the invention by mixing the following ingredients:

| | |
|---|---|
| Aluminum tris-(N-oxypyridinethiolate) | 0.1 g |
| Aluminum tri-(camphor-10-sulphonate) | 0.2 g |
| Perfume | 0.1 g |
| Colorant | 0.1 g |
| 50% strength ethyl alcohol q.s.p. | 100 ml |

EXAMPLE 15

An antiseptic cream is prepared according to the invention by mixing the following ingredients:

| | |
|---|---|
| Aluminum tris-(N-oxypyridinethiolate) | 0.2 g |
| Aluminum tri-(camphor-10-sulphonate) | 0.2 g |
| Glycol stearate | 1 g |
| Cetyl alcohol | 4 g |
| Polyoxyethylene stearate containing 20 mols of ethylene oxide | 6 g |
| Isopropyl palmitate | 10 g |
| Calophyllum oil | 1 g |
| Perfume q.s. | |
| Sterilised demineralised water | 100 g |

EXAMPLE 16

A dermatological block is prepared according to the invention by mixing the following ingredients:

| | |
|---|---|
| Aluminum tris-(N-oxypyridinethiolate) | 0.1 g |
| "Igepon A": sodium alkanesulphonate (GAF) | 81.5 g |
| Lantrol: liquid fraction of lanoline (Malmstrom) | 12 g |
| Perhydrosqualene | 2 g |
| Titanium dioxide | 2 g |
| Perfume | 2.5 g |

EXAMPLE 17

An antiseptic lotion for the skin is prepared according to the invention by mixing the following ingredients:

| | |
|---|---|
| Aluminum tris-(N-oxypyridinethiolate) | 0.7 g |
| Aluminum tri-(camphor-10-sulphonate) | 2.5 g |
| Ethyl alcohol | 13 ml |
| Polyethylene glycol | 10 g |
| Perfume q.s. | |
| Soluble colorants q.s. | |
| Sterilised demineralised water q.s.p. | 100 g |

EXAMPLE 18

A liquid anti-dandruff shampoo is prepared according to the invention by mixing the following ingredients:

| | |
|---|---|
| 4 mols of glycerol | 15 g |
| Quaternized copolymer of vinylpyrrolidone (Gafquat 755 from GAF) | 0.4 g |
| Aluminum tris-(N-oxypyridinethiolate) | 0.5 g |
| Aluminum tri-(camphor-10-sulphonate) | 1 g |
| Polyoxyethyleneated alkylamine marketed under the name Ethomeen 18/15 (Rhone Progil) | 0.8 g |
| Lactic acid q.s. pH 5 | |
| Perfume q.s. | |
| Water q.s.p. | 100 ml |

Regular application of this shampoo once or twice per week makes it possible to considerably reduce the formation of dandruff.

EXAMPLE 19

Granules, to be chewed, for countering parasites or microbial infections are prepared according to the invention by mixing the following ingredients:

| | |
|---|---|
| Sucrose | 200 g |
| Syrup of lemon | 50 g |
| Aluminum tris-(N-oxypyridinethiolate) | 0.4 g |

EXAMPLE 20

Anti-parasitic and antiseptic dragees, to be swallowed, are prepared according to the invention by mixing the following ingredients:

| | |
|---|---|
| Aluminum tris-(N-oxypyridinethiolate | 5 mg |
| Lactose | 300 mg |
| Powdered gum arabic | 100 mg |
| Simple syrup q.s.p. | 500 mg |

All forms of parasitosis are treated effectively by administering these dragees at the rate of two per day.

EXAMPLE 21

An antiseptic block is prepared according to the invention by mixing the following ingredients:

| | |
|---|---|
| Sodium salt of the isethionate ester of copra fatty acids, RCOOCH$_2$CH$_2$SO$_3$Na (R = derived from fatty acids having 12 to 18 carbon atoms | 74 g |
| Derivatives of lanoline and lecithin | 23 g |
| Aluminum tris-(N-oxypyridinethiolate) | 1 g |

EXAMPLE 22

An anti-dandruff and anti-parasitic powder shampoo is prepared according to the invention by mixing the following ingredients:

| | |
|---|---|
| Sodium lauryl-sulphate | 50 g |
| Sodium salt of isethionate esters of copra fatty acids, of the formula RCOOCH$_2$CH$_2$SO$_3$Na in which R represents $C_5$–$c_{17}$ radicals | 41 g |
| Aluminum tris-(N-oxypyridinethiolate) | 5 g |
| Perfme q.s. | 1 g |

At the time of use, the powder is dissolved in 10 times its weight of water.

EXAMPLE 23

An anti-dandruff liquid shampoo is prepared according to the invention by mixing the following ingredients:

| | |
|---|---|
| Polyoxyethyleneated lauryl alcohol (containing 12 mols of ethylene oxide) | 13 g |
| Copra diethanolamide | 4 g |
| quaternized copolymer of vinylpyrrolidone (Gafquat 755) | 0.4 g |
| Aluminum tris-(N-oxypyridinethiolate) | 0.3 g |
| Lactic acid q.s.p. pH 5 | |
| Perfume q.s. | |
| Water q.s.p. | 100 ml |

EXAMPLE 24

A face-treatment pack is prepared according to the invention by mixing the following ingredients:

| | |
|---|---|
| Oxyethyleneated lanoline | 5 g |
| Cetyl alcohol | 2 g |

| -continued | |
|---|---|
| Self-emulsifying ethylene glycol stearate | 7 g |
| Codex vaseline | 5 g |
| Kaolin | 10 g |
| Titanium oxide | 8 g |
| Aluminum tris-(N-oxypyridinethiolate) | 0.15 g |
| Water q.s.p. | 100 g |

EXAMPLE 25

An anti-mycosis and anti-acne gel is prepared according to the invention by mixing the following ingredients:

| | |
|---|---|
| Polymethacrylic acid sold under the name Carbopol 940 | 1.5 g |
| Aluminum tris-(N-oxypyridinethiolate) | 0.9 g |
| Aluminum tri-(camphor-10-sulphonate) | 3.2 g |
| Propylene glycol | 5 g |
| Triethanolamine q.s.p. pH 5 | |
| Water q.s.p. | 100 g |

We claim:
1. Aluminum tris-(N-oxypyridine-2-thiolate) of the following formula:

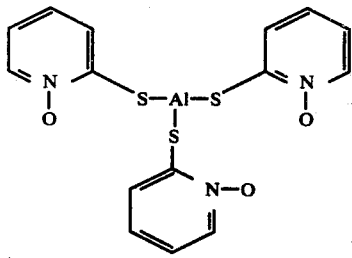

2. A cosmetic composition having deodorant, disinfectant and antiseptic activity comprising in a suitable vehicle an effective amount of aluminum tris-(N-oxypyrridine-2 thiolate).

3. A pharmaceutical composition for warm-blooded animals including man useful in the treatment of pityriasis, onyxis, intertrigos, dermatomycosis, dermatophytosis, impetigo, dermatosis with secondary infection, athletes foot, pruritus of infectious origin, hyperhidrosis or parasitosis, comprising in a suitable vehicle an effective amount of aluminum tris-(N-oxypyridine-2 thiolate).

4. A method for the treatment of pityriasis, onyxis, intertrigos, dermatomycosis, dermatophytosis, impetigo, dermatosis with a secondary infection, athletes foot, pruritus of infectious origin, hyperhidrosis, or parasitosis, which comprises administering in a suitable vehicle an effective amount of aluminum tris-(N-oxypyridine-2 thiolate).

5. Method according to claim 4 in which the said aluminum tris-(N-oxypyridine-2-thiolate) is administered topically or orally in a dose of 0.001 to 200.

6. Composition according to claim 2, in which the aluminum tris-(N-oxypyridine-2-thiolate) is present in an amount of 0.01 to 10% by weight based on the total weight of the composition.

7. Composition according to claim 6 in which the aluminum tris-(N-oxypyridine-2-thiolate) is present in an amount of 0.05 to 3% by weight based on the total weight of the composition.

8. Composition according to claim 2, which also contains aluminum tri-(camphor-10-sulphonate).

9. Composition according to claim 8, in which the aluminum tri-(camphor-10-sulphonate) is present in an amount of 0.05 to 30% by weight, based on the total weight of the composition.

10. Composition according to claim 3, in the form of tablets, dragees, capsules, pills, powder, granules, sugar-coated capsules, boles, potions, suspensions or solutions.

11. Composite feedstuff for animal feeding, comprising, as an additive in an edible excipient, aluminum tris-(N-oxypyridine-2-thiolate).

12. Feedstuff according to claim 11, in which the aluminum tris-(N-oxypyridine-2-thiolate) is present in an amount of between 1 and 2,000 ppm by weight.

13. Composition according to claim 3, in which the aluminum tris-(N-oxypyridine-2-thiolate) is present in an amount of 0.01 to 80% by weight, based on the total weight of the composition.

14. Composition according to claim 13, also comprising aluminum tri-(camphor-10-sulphonate).

15. Composition according to claim 14, in which the aluminum tri-(camphor-10-sulphonate) is present in an amount of 0.05 to 30% by weight, based on the total weight of the composition.

REEXAMINATION CERTIFICATE (1468th)
United States Patent [19]
Bouillon et al.

[11] B1 4,209,506

[45] Certificate Issued May 21, 1991

[54] ALUMINUM TRIS-(N-OXYPYRIDINE-2-THIOLATE); COSMETIC OR PHARMACEUTICAL COMPOSITIONS CONTAINING THE SAME AND THE USE OF SAID COMPOSITIONS

[75] Inventors: Claude Bouillon, Eaubonne; Georges Rosenbaum, Asnieres, both of France

[73] Assignee: Societe Anonyme dite: L'Oreal

Reexamination Request:
No. 90/001,639, Nov. 18, 1988

Reexamination Certificate for:
  Patent No.: 4,209,506
  Issued: Jun. 24, 1980
  Appl. No.: 928,312
  Filed: Jul. 26, 1978

[51] Int. Cl.$^5$ .................. C07D 213/89; A61K 31/44; A61K 7/38
[52] U.S. Cl. ........................................ 424/68; 424/46; 424/47; 424/69; 424/70; 424/DIG. 5; 426/532; 514/335; 514/191; 546/6
[58] Field of Search .................... 546/6; 514/191, 335; 424/68, 47, 69, 70; 426/532

[56] References Cited

U.S. PATENT DOCUMENTS

| | | | |
|---|---|---|---|
| 2,809,971 | 10/1957 | Bernstein | 546/3 |
| 3,236,733 | 2/1966 | Karsten | 514/188 |
| 3,347,863 | 10/1967 | Ottmann | 546/6 |
| 3,752,812 | 8/1973 | Abushanab | 544/354 |
| 3,785,985 | 1/1974 | Grand | 514/188 |
| 3,949,079 | 4/1976 | Brandl | 424/122 |
| 3,950,350 | 4/1976 | Hammen | 540/311 |
| 3,950,515 | 4/1976 | Waite | 424/115 |

FOREIGN PATENT DOCUMENTS 48-65240  9/1973  Japan .

*Primary Examiner*—Mark L. Berch

[57] ABSTRACT

Aluminum tris(N-oxypyridine-2-thiolate) is useful in the prophylaxis or treatment of any pathological manifestation in which the presence of a microorganism is involved. It is a new compound made by the reaction of aluminum isopropylate with the N-oxide of pyridine-2-thiol.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-15 are cancelled.

New claims 16-23 are added and determined to be patentable.

*16. A cosmetic composition having deodorant, disinfectant and antiseptic activity comprising in a suitable vehicle an effective amount of aluminum tris-(N-oxypyridine-2-thiolate) and aluminum tri (camphor-10-sulphonate).*

*17. The cosmetic composition of claim 16 in which the aluminum tri (camphor-10-sulphonate) is present in an amount of 0.05 to 30% by weight, based on the total weight of the composition.*

*18. The cosmetic composition of claim 16 in which the aluminum tris-(N-oxypyridine-2-thiolate) is present in an amount of 0.05 to 3% by weight based on the total weight of the composition.*

*19. A pharmaceutical composition for warm-blooded animals including man useful in the treatment of pityriasis, onyxis, intertrigos, dermatomycosis, dermatophytosis, impetigo, dermatosis with secondary infection, athletes foot, pruritus of infectious origin, hyperhidrosis or parasitosis, comprising in a suitable vehicle an effective amount of aluminum tris-(N-oxypyridine-2-thiolate) and aluminum tri-(camphor-10-sulphonate).*

*20. The pharmaceutical composition of claim 19 in which the aluminum tri-(camphor-10-sulphonate) is present in an amount of 0.05 to 30% by weight, based on the total weight of the composition.*

*21. The cosmetic composition of claim 16 in which the aluminum tris-(N-oxypyridine-2-thiolate) is present in an amount of 0.01 to 10% by weight based on the total weight of the composition.*

*22. The pharmaceutical composition of claim 19 for oral administration in which the aluminum tris-(N-oxypyridine-2-thiolate) is present in an amount of 0.01 to 80% weight, based on the total weight of the composition.*

*23. The pharmaceutical composition of claim 19 for local administration in which the aluminum tris-(N-oxypyridine-2-thiolate) is present in an amount of 0.01 to 10% by weight, based on the total weight of the composition.*

* * * * *